US012599585B2

(12) United States Patent
Kamin et al.

(10) Patent No.: US 12,599,585 B2
(45) **Date of Patent: *Apr. 14, 2026**

(54) USE OF [(1R)-1-(2-CHLOROPHENYL)-2-(TETRAZOL-2-YL)ETHYL] CARBAMATE IN COMBINATION THERAPY

(71) Applicant: SK BIOPHARMACEUTICALS CO., LTD., Gyeonggi-do (KR)

(72) Inventors: Marc Kamin, South Fair Lawn, NJ (US); Laurent Vernillet, South Fair Lawn, NJ (US)

(73) Assignee: SK BIOPHARMACEUTICALS CO., LTD., Gyeonggi-do (KR)

( * ) Notice: Subject to any disclaimer, the term of this patent is extended or adjusted under 35 U.S.C. 154(b) by 434 days.

This patent is subject to a terminal disclaimer.

(21) Appl. No.: 18/134,203

(22) Filed: Apr. 13, 2023

(65) Prior Publication Data

US 2023/0293489 A1 Sep. 21, 2023

Related U.S. Application Data

(63) Continuation of application No. 17/037,932, filed on Sep. 30, 2020, now Pat. No. 11,654,133, which is a continuation of application No. 16/348,630, filed as application No. PCT/KR2019/003294 on Mar. 21, 2019, now abandoned.

(60) Provisional application No. 62/646,043, filed on Mar. 21, 2018.

(51) Int. Cl.

| | |
|---|---|
| ***A61K 31/41*** | (2006.01) |
| ***A61K 31/4166*** | (2006.01) |
| ***A61K 31/515*** | (2006.01) |
| ***A61K 31/53*** | (2006.01) |
| ***A61K 31/55*** | (2006.01) |
| ***A61P 25/08*** | (2006.01) |

(52) U.S. Cl.

CPC .......... *A61K 31/41* (2013.01); *A61K 31/4166* (2013.01); *A61K 31/515* (2013.01); *A61K 31/53* (2013.01); *A61K 31/55* (2013.01); *A61P 25/08* (2018.01)

(58) Field of Classification Search

CPC ...... A61K 31/41; A61K 31/515; A61K 31/19; A61K 31/4015; A61K 31/4166; A61K 31/53; A61K 31/55; A61K 45/06; A61P 25/00; A61P 25/08

See application file for complete search history.

(56) References Cited

FOREIGN PATENT DOCUMENTS

WO WO-2017/075222 A1 5/2017

OTHER PUBLICATIONS

Majid et al., "Impact of perampanel on pharmacokinetics of concomitant antiepileptics in patients with partial-onset seizures: pooled analysis of clinical trials", Br J Cln Pharmacol, 2016, 82, pp. 422-430. (Year: 2016).*

Tolman et al., "Treatment options for refractory and difficult to treat seizures: focus on vigabatrin", Therapeutics and Clinical Risk Management, Aug. 31, 2011. (Year: 2011).*

Nakmura et al. "Mechanism of Action of Cenobamate: Preferential Inhibition of the Persistent Sodium Current", Apr. 10, 2018, 90, 15 supplement PS 278. (Year: 2018).*

Margoilis et al., "Effectiveness of Antiepileptic Drug Combination Therapy for Partial-Onset Seizures Based on Mechanisms of Action", JAMA Neurol, 2014, 71, (8), pp. 985-993. (Year: 2014).*

International Search Report from corresponding PCT Application No. PCT/KR2019/003294, mailed on Jul. 3, 2019.

"[Viva100] SK Biopharm's new antiepileptic drug, 'Cenobamate' is about to be commercialized . . . It aims at 1 trillion won in annual sales, the world's No. 1 'Vimpat'." BridgeEconomic (Online newspaper), Dec. 7, 2017, pp. 1-3, Retrieved from <URL: http://www.viva100.com/main/view.php?key=20171205010001659>.

Krauss, Gregory et al., "Seizure freedom with YKP3089as adjunctive therapy for refractory partial-onset seizures in double-blind placebocontrolled trials (P2.019)." Neurology, 2016, vol. 86, Suppl. 16, Retrieved from <URL: https://n.neurology.org/content/86/16_Supplement/P2.019>.

Zaccara, Gaetano et al., "Interactions between antiepileptic drugs, and between antiepileptic drugs and other drugs." Epileptic Disorders, 2014, vol. 16, No. 4, pp. 409-431.

Vernillet, L. et al., "Drug-drug interactions between cenobamate and other antiepileptic drugs: Results from phase 1 studies with carbamazepine, phenobarbital, phenytoin, and divalproex sodium." American Society for Clinical Pharmacology & Therapeutics, Abstracts of 2018 Annual Meeting; Mar. 21-24, 2018 (First published: Feb. 7, 2018), Orlando, FL., USA, pp. S5-S97.

Sperling, M. R., et al.; "Safety of Cenobamate (YKP3089) as Adjunctive Treatment for Uncontrolled Partial (Focal) Seizures: Results From a Large, Phase 3, Multicenter, Open-Label Study", Presented at the American Epilepsy Society Annual Meeting, Nov. 30-Dec. 4, 2018, New Orleans, LA, USA, poster.

Kamin, M., et al.; "Time to Onset of Efficacy in Seizure Reduction With Cenobamate (YKP3089) in Patients With Uncontrolled Partial Seizures From Two Randomized Clinical Trials", Presented at the American Epilepsy Society Annual Meeting, Nov. 30-Dec. 4, 2018, New Orleans, LA, USA, poster.

Incecayir, T., et al.; "Bioavailability File: Lamotrigine", FABAD J. Pharm. Sci., 31, pp. 163-179, 2006.

Rojanasthien, N., et al.; "Effect of Doses on the Bioavailability of Phenytoin from a Prompt-Release and an Extended-Release Preparation: Single Dose Study", J Med Assoc Thai 2007; 90 (9): 1883-93.

(Continued)

*Primary Examiner* — Brian-Yong S Kwon

(74) *Attorney, Agent, or Firm* — Harness, Dickey & Pierce, P.L.C.

(57) ABSTRACT

The present disclosure provides combination therapy using [(1R)-1-(2-chlorophenyl)-2-(tetrazol-2-yl)ethyl] carbamate (cenobamate) and one or more antiepileptic drugs for the prevention or treatment of a neurological disorder such as epilepsy.

5 Claims, 3 Drawing Sheets

(56) References Cited

OTHER PUBLICATIONS

Vernillet, L., et al.; "Drug-Drug Interactions Between Cenobamate and Other Antiepileptic Drugs: Results From Phase I Studies With Carbamazepine, Phenobarbital, Phenytoin, and Divalproex Sodium", Presented at the Annual Meeting of the American Society for Clinical Pharmacology & Therapeutics (ASCPT 2018), Mar. 21-24, 2018, Orlando, FL., poster.

Golyala et al., "Drug development for refractory epilepsy: The past 25 years and beyond", Seizure, 2017, vol. 44, pp. 147-156.

Office Action (Non-Final) from corresponding U.S. Appl. No. 16/348,630,, dated Apr. 1, 2020.

Reynolds, E. H., et al.; "Single Drug or Combination Therapy for Epilepsy?", Drugs, 1981, vol. 21, pp. 374-382.

Zaccara, G., et al.; "Antiepileptic Drugs in Clinical Development: Differentiate or Die?", Current Pharmaceutical Design., 2017, vol. 23, pp. 5593-5605.

Extended European Search Report from corresponding European Patent Application No. 19771303.5, dated Dec. 9, 2021.

Office Action from corresponding U.S. Appl. No. 17/037,932, dated May 25, 2022.

Notice of Allowance from corresponding U.S. Appl. No. 17/037,932, dated Jan. 19, 2023.

SK Life Science, "Safety and Pharmacokinetic Study of YKP3089 as Adjunctive Therapy in Subjects with Partial Onset Seizures—NCT02535091," ClinicalTrials.gov, Jun. 16, 2017.

EP Communication from corresponding European Patent Application No. 19 771 303.5, dated May 31, 2024.

* cited by examiner

USE OF [(1R)-1-(2-CHLOROPHENYL)-2-(TETRAZOL-2-YL)ETHYL] CARBAMATE IN COMBINATION THERAPY

CROSS-REFERENCE TO RELATED APPLICATIONS

This application is a continuation of U.S. application Ser. No. 17/037,932, filed on May 25, 2022, which is a continuation of U.S. application Ser. No. 16/348,630, filed on May 9, 2019, which is a national phase application of PCT Application No. PCT/KR2019/003294, filed on Mar. 21, 2019, which claims the benefit and priority to U.S. Provisional Patent Application No. 62/646,043, filed on Mar. 21, 2018. The entire disclosures of the applications identified in this paragraph are incorporated herein by references.

FIELD

The present disclosure relates to use of [(1R)-1-(2-chlorophenyl)-2-(tetrazol-2-yl)ethyl] carbamate (cenobamate) of the following Formula 1 in a combination therapy for the prevention or treatment of a neurological disorder such as epilepsy:

[Formula 1]

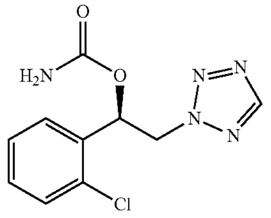

BACKGROUND

Epilepsy is a group of neurological disorders characterized by epileptic seizures. The exact mechanism of epilepsy is unknown. Epileptic seizures are the result of excessive and abnormal neuronal activity in the cortex of the brain.

It has been known that large proportions (about 20%-40%) of epilepsy patients continue to experience uncontrolled seizures despite treatment with antiepileptic drugs (AEDs). Treatment regimens for these refractory patients often include 2 to 4 different AEDs of long-term adjunctive therapy and multiple AEDs are highly susceptible to drug interactions. Most AEDs have narrow therapeutic indices and thus modifications in their pharmacokinetics (PK) may result in treatment failure or safety concerns. Determining how AEDs act on disease, their side effects, and elucidating any potential risks to patients is not a simple process.

Cenobamate, a novel compound which has been developed for the treatment of adults with partial onset seizures, is known for having a potentially unique dual mechanism of action.

DISCLOSURE

Technical Problem

The present disclosure is intended to assess the effect of cenobamate on the disposition of antiepileptic drugs in patients.

In addition, the present disclosure is intended to assess the effect of each AED on the disposition of cenobamate.

Furthermore, the present disclosure is intended to evaluate the safety and tolerability of each AED in combination with cenobamate in patients.

Furthermore, the present disclosure is intended to provide a method for treating patients suffering from a neurological disorder such as epilepsy in which side effects at the time of co-administering cenobamate with one or more antiepileptic drugs are alleviated and maximum safety can be obtained by assessing the above items.

Solution to Problem

The present disclosure provides a method of using cenobamate for treating a patient who is suffering from a neurological disorder such as epilepsy. With the advent of multiple AEDs, examining drug effects in the context of combination AED therapy and determining potential toxicities and dose adjustments is thus critical when developing any new treatment for these patients. In the present disclosure, at the time of co-administering a therapeutically effective amount of cenobamate and one or more antiepileptic drugs, side effects are alleviated and maximum safety can be obtained by adjusting the dose of cenobamate and/or one or more antiepileptic drugs.

In one embodiment of the present disclosure, there is provided a method for treating a patient who is suffering from epilepsy with co-administering a therapeutically effective amount of (i) [(1R)-1-(2-chlorophenyl)-2-(tetrazol-2-yl)ethyl] carbamate (cenobamate) of the following Formula 1 or a pharmaceutically acceptable salt thereof and (ii) one or more antiepileptic drugs, said method comprising: modifying the therapeutically effective amount of the antiepileptic drug to adjust AUC of the antiepileptic drug obtained after the co-administration having at least 5% difference to the level of AUC obtained after the administration of antiepileptic drug to the patient without cenobamate or a pharmaceutically acceptable salt thereof:

[Formula 1]

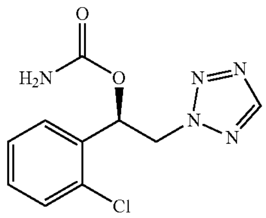

wherein the therapeutically effective amount of cenobamate or a pharmaceutically acceptable salt thereof is from about 100 mg/day to about 400 mg/day.

In another embodiment of the present disclosure, there is provided a method for treating a patient who is suffering from epilepsy with co-administering a therapeutically effective amount of (i) cenobamate or a pharmaceutically acceptable salt thereof and (ii) phenytoin, said method comprising: increasing the therapeutically effective amount of cenobamate to compensate about 20% to about 40% reduction in AUC of cenobamate obtained after the co-administration to the level of AUC obtained after the administration of cenobamate to the patient without phenytoin.

In still another embodiment of the present disclosure, there is provided a pharmaceutical composition for the prevention or treatment of epilepsy, comprising a therapeutically effective amount of (i) cenobamate or a pharmaceutically acceptable salt thereof and (ii) one or more antiepileptic drugs, wherein the therapeutically effective amount of the antiepileptic drug is modified to adjust AUC of the antiepileptic drug obtained after the co-administration having at least 5% difference to the level of AUC obtained after the administration of antiepileptic drug to the patient without cenobamate or a pharmaceutically acceptable salt thereof.

In still another embodiment of the present disclosure, there is provided a pharmaceutical composition for the prevention or treatment of epilepsy, comprising a therapeutically effective amount of (i) cenobamate or a pharmaceutically acceptable salt thereof and (ii) phenytoin, wherein the therapeutically effective amount of cenobamate is increased to compensate about 20% to about 40% reduction in AUC of cenobamate obtained after the co-administration to the level of AUC obtained after the administration of cenobamate to the patient without phenytoin.

In still another embodiment of the present disclosure, there is provided use of a pharmaceutical composition comprising a therapeutically effective amount of (i) cenobamate or a pharmaceutically acceptable salt thereof and (ii) one or more antiepileptic drugs in the prevention or treatment of epilepsy, wherein the therapeutically effective amount of the antiepileptic drug is modified to adjust AUC of the antiepileptic drug obtained after the co-administration having at least 5% difference to the level of AUC obtained after the administration of antiepileptic drug to the patient without cenobamate or a pharmaceutically acceptable salt thereof.

In still another embodiment of the present disclosure, there is provided use of a pharmaceutical composition comprising a therapeutically effective amount of (i) cenobamate or a pharmaceutically acceptable salt thereof and (ii) phenytoin in the prevention or treatment of epilepsy, wherein the therapeutically effective amount of cenobamate is increased to compensate about 20% to about 40% reduction in AUC of cenobamate obtained after the co-administration to the level of AUC obtained after the administration of cenobamate to the patient without phenytoin.

Herein, therapeutically effective amount of cenobamate and other antiepileptic drugs is described on the basis of administering an immediate release oral dosage form to an adult, and thus that of cenobamate and antiepileptic drugs may vary in the case of administering other dosage forms such as intravenous injection or extended-release dosage form, or administering to children under the age of 13. The term "immediate" release should mean that the formulation does release the full dose of the active ingredient immediately after oral dosing dependent or independent from the pH value.

As used herein, the term "about" means±20%, 10% or 5% of the indicated range or value, unless otherwise indicated.

As used herein, the term "epilepsy" refers to a neurological disorder which includes epileptic seizure, focal seizure, generalized seizure, acute symptomatic seizure, idiopathic epilepsy, symptomatic epilepsy and cryptogenic epilepsy. In addition, epilepsy may be partial onset seizure with/without secondary generalization.

As used herein, the term "co-administration" means that cenobamate or a pharmaceutically acceptable salt thereof and one or more antiepileptic drugs may be administered simultaneously, subsequently or separately.

As used herein, the term "therapeutically effective amount" means that amount of cenobamate or a pharmaceutically acceptable salt thereof and one or more antiepileptic drugs that is non-toxic but sufficient to elicits the biological or medicinal response in patients. Therefore, a "therapeutically effective amount" may be dependent in some instances on such biological factors. Further, while the achievement of therapeutic effects may be measured by a physician or other qualified medical personnel using evaluations known in the art, it is recognized that individual variation and response to treatments may make the achievement of therapeutic effects a somewhat subjective decision. The determination of an effective amount is well within the ordinary skill in the art of pharmaceutical sciences and medicine.

As used herein, the term "dose" refers to the measured quantity of cenobamate or a pharmaceutically acceptable salt thereof and one or more antiepileptic drugs that be administered to patients at one time.

As used herein, pharmacokinetic parameters refer to in vivo characteristics of cenobamate or a pharmaceutically acceptable salt thereof and one or more antiepileptic drugs over time. These parameters include plasma concentration (C), as well as Cmin, Cavg, Cmax and AUC. The term "AUC" is the area under the curve of a graph of the measured plasma concentration of an active agent vs. time, measured from one time point to another time point. The term "AUC" used herein refers the area under the curve of plasma concentration in each dosing interval at steady state (i.e., from time of initial administration of drug to time t, where t is the length of the dosing interval).

As used herein, the term "optionally" means that the subsequently described event or circumstance may or may not occur, and that the description includes instances where said event or circumstance occurs and instances in which it does not.

One embodiment of the present disclosure is a method for treating a patient who is suffering from epilepsy with co-administering a therapeutically effective amount of (i) cenobamate or a pharmaceutically acceptable salt thereof and (ii) one or more antiepileptic drugs, said method comprising:

modifying the therapeutically effective amount of the antiepileptic drug to adjust AUC of the antiepileptic drug obtained after the co-administration having at least 5% difference to the level of AUC obtained after the administration of antiepileptic drug to the patient without cenobamate or a pharmaceutically acceptable salt thereof, wherein the therapeutically effective amount of cenobamate or a pharmaceutically acceptable salt thereof is from about 100 mg/day to about 400 mg/day.

In one embodiment, the antiepileptic drug may be selected from the group consisting of carbamazepine, lamotrigine, phenobarbital and phenytoin.

In one embodiment, the therapeutically effective amount of cenobamate may be from about 100 mg/day to about 400 mg/day.

In one embodiment, the therapeutically effective amount of cenobamate may be achieved by the following titration method:

(1) administering cenobamate to the patient about 12.5 mg once daily for about two weeks;

(2) then administering cenobamate to the patient about 25 mg once daily for two weeks;

(3) then administering cenobamate to the patient about 50 mg once daily for about two weeks; and (4) then increasing the dose in about bi-weekly increments by no more than about 50 mg once daily to a therapeutically effective amount.

In one embodiment, the therapeutically effective amount of cenobamate may be achieved by the following titration method:

(1) administering cenobamate to the patient about 50 mg once daily for about two weeks; and (2) then increasing the dose in about bi-weekly increments by about 50 mg once daily to about 200 mg/day once daily, wherein cenobamate is administered for about 6 weeks and the therapeutically effective amount of cenobamate is about 200 mg/day.

In one embodiment, the therapeutically effective amount of cenobamate may be achieved by the following titration method:

(1) administering cenobamate to the patient about 50 mg once daily which is increased with 50 mg once daily per week to about 100 mg/day;

(2) optionally increasing the dose in about weekly increments by about 50 mg once daily per week to about 200 mg/day; and (3) optionally increasing the dose in about weekly increments by about 100 mg/day per week to about 400 mg/day, wherein cenobamate is administered for about 2 weeks, 4 weeks or 6 weeks depending on therapeutically effective amount of cenobamate which is required and the therapeutically effective amount of cenobamate is about 100 mg/day, about 200 mg/day or about 400 mg/day.

Because the therapeutically effective amount of cenobamate may vary depending on the status of patients, the optional step(s) may be carried out or not.

In one embodiment, the antiepileptic drug may be carbamazepine.

In one embodiment, a therapeutically effective amount of carbamazepine in case of its monotherapy may be from about 800 mg/day to about 1,200 mg/day.

In one embodiment, the therapeutically effective amount of carbamazepine may be increased by about 5 to 40% by weight, 5 to 39% by weight, 5 to 38% by weight, 5 to 37% by weight, 5 to 36% by weight, 5 to 35% by weight, 5 to 34% by weight, 6 to 40% by weight, 6 to 39% by weight, 6 to 38% by weight, 6 to 37% by weight, 6 to 36% by weight, 6 to 35% by weight, 6 to 34% by weight, 7 to 40% by weight, 7 to 39% by weight, 7 to 38% by weight, 7 to 37% by weight, 7 to 36% by weight, 7 to 35% by weight, 7 to 34% by weight, 8 to 40% by weight, 8 to 39% by weight, 8 to 38% by weight, 8 to 37% by weight, 8 to 36% by weight, 8 to 35% by weight, 8 to 34% by weight, 9 to 40% by weight, 9 to 39% by weight, 9 to 38% by weight, 9 to 37% by weight, 9 to 36% by weight, 9 to 35% by weight, 9 to 34% by weight, 10 to 40% by weight, 10 to 39% by weight, 10 to 38% by weight, 10 to 37% by weight, 10 to 36% by weight, 10 to 35% by weight, 10 to 34% by weight, 11 to 40% by weight, 11 to 39% by weight, 11 to 38% by weight, 11 to 37% by weight, 11 to 36% by weight, 11 to 35% by weight or 11 to 34% by weight, compared to a therapeutically effective amount of the patient in case of its monotherapy.

In one embodiment, the therapeutically effective amount of carbamazepine may be increased to compensate about 5 to 40%, 5 to 39%, 5 to 38%, 5 to 37%, 5 to 36%, 5 to 35%, 5 to 34%, 6 to 40%, 6 to 39%, 6 to 38%, 6 to 37%, 6 to 36%, 6 to 35%, 6 to 34%, 7 to 40%, 7 to 39%, 7 to 38%, 7 to 37%, 7 to 36%, 7 to 35%, 7 to 34%, 8 to 40%, 8 to 39%, 8 to 38%, 8 to 37%, 8 to 36%, 8 to 35%, 8 to 34%, 9 to 40%, 9 to 39%, 9 to 38%, 9 to 37%, 9 to 36%, 9 to 35%, 9 to 34%, 10 to 40%, 10 to 39%, 10 to 38%, 10 to 37%, 10 to 36%, 10 to 35%, 10 to 34%, 11 to 40%, 11 to 39%, 11 to 38%, 11 to 37%, 11 to 36%, 11 to 35% or 11 to 34% reduction in AUC of carbamazepine obtained after the co-administration to the level of AUC obtained after the administration of carbamazepine to the patient without cenobamate.

In one embodiment, the antiepileptic drug may be lamotrigine.

In one embodiment, the therapeutically effective amount of lamotrigine may be increased by about 7 to 140% by weight, 7 to 139% by weight, 7 to 138% by weight, 7 to 137% by weight, 7 to 136% by weight, 7 to 135% by weight, 7 to 134% by weight, 7 to 133% by weight, 7 to 132% by weight, 7 to 131% by weight, 7 to 130% by weight, 7 to 129% by weight, 7 to 128% by weight, 7 to 127% by weight, 7 to 126% by weight, 7 to 125% by weight, 7 to 124% by weight, 7 to 123% by weight, 7 to 122% by weight, 7 to 121% by weight, 7 to 120% by weight, 7 to 119% by weight, 7 to 118% by weight, 7 to 117% by weight, 7 to 116% by weight, 7 to 115% by weight, 7 to 114% by weight, 7 to 113% by weight, 7 to 112% by weight, 7 to 111% by weight, 7 to 110% by weight, 7 to 109% by weight, 7 to 108% by weight, 7 to 107% by weight, 7 to 106% by weight, 7 to 105% by weight, 7 to 104% by weight, 7 to 103% by weight, 7 to 102% by weight, 7 to 101% by weight, 7 to 100% by weight, 7 to 99% by weight, 7 to 98% by weight, 7 to 97% by weight, 7 to 96% by weight, 7 to 95% by weight, 7 to 94% by weight, 7 to 93% by weight, 8 to 140% by weight, 8 to 139% by weight, 8 to 138% by weight, 8 to 137% by weight, 8 to 136% by weight, 8 to 135% by weight, 8 to 134% by weight, 8 to 133% by weight, 8 to 132% by weight, 8 to 131% by weight, 8 to 130% by weight, 8 to 129% by weight, 8 to 128% by weight, 8 to 127% by weight, 8 to 126% by weight, 8 to 125% by weight, 8 to 124% by weight, 8 to 123% by weight, 8 to 122% by weight, 8 to 121% by weight, 8 to 120% by weight, 8 to 119% by weight, 8 to 118% by weight, 8 to 117% by weight, 8 to 116% by weight, 8 to 115% by weight, 8 to 114% by weight, 8 to 113% by weight, 8 to 112% by weight, 8 to 111% by weight, 8 to 110% by weight, 8 to 109% by weight, 8 to 108% by weight, 8 to 107% by weight, 8 to 106% by weight, 8 to 105% by weight, 8 to 104% by weight, 8 to 103% by weight, 8 to 102% by weight, 8 to 101% by weight, 8 to 100% by weight, 8 to 99% by weight, 8 to 98% by weight, 8 to 97% by weight, 8 to 96% by weight, 8 to 95% by weight, 8 to 94% by weight, 8 to 93% by weight, 9 to 140% by weight, 9 to 139% by weight, 9 to 138% by weight, 9 to 137% by weight, 9 to 136% by weight, 9 to 135% by weight, 9 to 134% by weight, 9 to 133% by weight, 9 to 132% by weight, 9 to 131% by weight, 9 to 130% by weight, 9 to 129% by weight, 9 to 128% by weight, 9 to 127% by weight, 9 to 126% by weight, 9 to 125% by weight, 9 to 124% by weight, 9 to 123% by weight, 9 to 122% by weight, 9 to 121% by weight, 9 to 120% by weight, 9 to 119% by weight, 9 to 118% by weight, 9 to 117% by weight, 9 to 116% by weight, 9 to 115% by weight, 9 to 114% by weight, 9 to 113% by weight, 9 to 112% by weight, 9 to 111% by weight, 9 to 110% by weight, 9 to 109% by weight, 9 to 108% by weight, 9 to 107% by weight, 9 to 106% by weight, 9 to 105% by weight, 9 to 104% by weight, 9 to 103% by weight, 9 to 102% by weight, 9 to 101% by weight, 9 to 100% by weight, 9 to 99% by weight, 9 to 98% by weight, 9 to 97% by weight, 9 to 96% by weight, 9 to 95% by weight, 9 to 94% by weight, 9 to 93% by weight, 10 to 140% by weight, 10 to 139% by weight, 10 to 138% by weight, 10 to 137% by weight, 10 to 136% by weight, 10 to 135% by weight, 10 to 134% by weight, 10 to 133% by weight, 10 to 132% by weight, 10 to 131% by weight, 10 to 130% by weight, 10 to 129% by weight, 10 to 128% by weight, 10 to 127% by weight, 10 to 126% by weight, 10 to 125% by weight, 10 to 124% by weight, 10 to 123% by weight, 10 to 122% by weight, 10 to 121% by weight, 10 to 120% by weight, 10 to 119% by weight, 10 to 118% by weight, 10 to 117% by weight, 10 to 116% by weight, 10 to 115% by weight, 10 to 114% by weight, 10 to 113% by weight, 10 to 112% by weight, 10 to 111% by weight, 10 to 110% by weight, 10 to 109% by weight, 10 to 108% by weight, 10 to 107% by weight, 10 to 106% by weight, 10 to 105% by weight, 10 to 104% by weight, 10 to 103% by weight, 10 to 102% by weight, 10 to 101% by weight, 10 to 100% by weight, 10 to 99% by weight, 10 to 98% by weight, 10 to 97% by weight, 10 to 96% by weight, 10 to 95% by weight, 10 to 94% by weight, 10 to 93% by weight, 11 to 140% by weight, 11 to 139% by weight, 11 to 138% by weight, 11 to 137% by weight, 11 to 136% by weight, 11 to 135% by weight, 11 to 134% by weight, 11 to 133% by weight, 11 to 132% by weight, 11 to 131% by weight, 11 to 130% by weight, 11 to 129% by weight, 11 to 128% by weight, 11 to 127% by weight, 11 to 126% by weight, 11 to 125% by weight, 11 to 124% by weight, 11 to 123% by weight, 11 to 122% by weight, 11 to 121% by weight, 11 to 120% by weight, 11 to 119% by weight, 11 to 118% by weight, 11 to 117% by weight, 11 to 116% by weight, 11 to 115% by weight, 11 to 114% by weight, 11 to 113% by weight, 11 to 112% by weight, 11 to 111% by weight, 11 to 110% by weight, 11 to 109% by weight, 11 to 108% by weight, 11 to 107% by weight, 11 to 106% by weight, 11 to 105% by weight, 11 to 104% by weight, 11 to 103% by weight, 11 to 102% by weight, 11 to 101% by weight, 11 to 100% by weight, 11 to 99% by weight, 11 to 98% by weight, 11 to 97% by weight, 11 to 96% by weight, 11 to 95% by weight, 11 to 94% by weight, 11 to 93% by weight, 12 to 140% by weight, 12 to 139% by weight, 12 to 138% by weight, 12 to 137% by weight, 12 to 136% by weight, 12 to 135% by weight, 12 to 134% by weight, 12 to 133% by weight, 12 to 132% by weight, 12 to 131% by weight, 12 to 130% by weight, 12 to 129% by weight, 12 to 128% by weight, 12 to 127% by weight, 12 to 126% by weight, 12 to 125% by weight, 12 to 124% by weight, 12 to 123% by weight, 12 to 122% by weight, 12 to 121% by weight, 12 to 120% by weight, 12 to 119% by weight, 12 to 118% by weight, 12 to 117% by weight, 12 to 116% by weight, 12 to 115% by weight, 12 to 114% by weight, 12 to 113% by weight, 12 to 112% by weight, 12 to 111% by weight, 12 to 110% by weight, 12 to 109% by weight, 12 to 108% by weight, 12 to 107% by weight, 12 to 106% by weight, 12 to 105% by weight, 12 to 104% by weight, 12 to 103% by weight, 12 to 102% by weight, 12 to 101% by weight, 12 to 100% by weight, 12 to 99% by weight, 12 to 98% by weight, 12 to 97% by weight, 12 to 96% by weight, 12 to 95% by weight, 12 to 94% by weight, 12 to 93% by weight, 13 to 140% by weight, 13 to 139% by weight, 13 to 138% by weight, 13 to 137% by weight, 13 to 136% by weight, 13 to 135% by weight, 13 to 134% by weight, 13 to 133% by weight, 13 to 132% by weight, 13 to 131% by weight, 13 to 130% by weight, 13 to 129% by weight, 13 to 128% by weight, 13 to 127% by weight, 13 to 126% by weight, 13 to 125% by weight, 13 to 124% by weight, 13 to 123% by weight, 13 to 122% by weight, 13 to 121% by weight, 13 to 120% by weight, 13 to 119% by weight, 13 to 118% by weight, 13 to 117% by weight, 13 to 116% by weight, 13 to 115% by weight, 13 to 114% by weight, 13 to 113% by weight, 13 to 112% by weight, 13 to 111% by weight, 13 to 110% by weight, 13 to 109% by weight, 13 to 108% by weight, 13 to 107% by weight, 13 to 106% by weight, 13 to 105% by weight, 13 to 104% by weight, 13 to 103% by weight, 13 to 102% by weight, 13 to 101% by weight, 13 to 100% by weight, 13 to 99% by weight, 13 to 98% by weight, 13 to 97% by weight, 13 to 96% by weight, 13 to 95% by weight, 13 to 94% by weight, 13 to 93% by weight, 14 to 140% by weight, 14 to 139% by weight, 14 to 138% by weight, 14 to 137% by weight, 14 to 136% by weight, 14 to 135% by weight, 14 to 134% by weight, 14 to 133% by weight, 14 to 132% by weight, 14 to 131% by weight, 14 to 130% by weight, 14 to 129% by weight, 14 to 128% by weight, 14 to 127% by weight, 14 to 126% by weight, 14 to 125% by weight, 14 to 124% by weight, 14 to 123% by weight, 14 to 122% by weight, 14 to 121% by weight, 14 to 120% by weight, 14 to 119% by weight, 14 to 118% by weight, 14 to 117% by weight, 14 to 116% by weight, 14 to 115% by weight, 14 to 114% by weight, 14 to 113% by weight, 14 to 112% by weight, 14 to 111% by weight, 14 to 110% by weight, 14 to 109% by weight, 14 to 108% by weight, 14 to 107% by weight, 14 to 106% by weight, 14 to 105% by weight, 14 to 104% by weight, 14 to 103% by weight, 14 to 102% by weight, 14 to 101% by weight, 14 to 100% by weight, 14 to 99% by weight, 14 to 98% by weight, 14 to 97% by weight, 14 to 96% by weight, 14 to 95% by weight, 14 to 94% by weight, 14 to 93% by weight, 15 to 140% by weight, 15 to 139% by weight, 15 to 138% by weight, 15 to 137% by weight, 15 to 136% by weight, 15 to 135% by weight, 15 to 134% by weight, 15 to 133% by weight, 15 to 132% by weight, 15 to 131% by weight, 15 to 130% by weight, 15 to 129% by weight, 15 to 128% by weight, 15 to 127% by weight, 15 to 126% by weight, 15 to 125% by weight, 15 to 124% by weight, 15 to 123% by weight, 15 to 122% by weight, 15 to 121% by weight, 15 to 120% by weight, 15 to 119% by weight, 15 to 118% by weight, 15 to 117% by weight, 15 to 116% by weight, 15 to 115% by weight, 15 to 114% by weight, 15 to 113% by weight, 15 to 112% by weight, 15 to 111% by weight, 15 to 110% by weight, 15 to 109% by weight, 15 to 108% by weight, 15 to 107% by weight, 15 to 106% by weight, 15 to 105% by weight, 15 to 104% by weight, 15 to 103% by weight, 15 to 102% by weight, 15 to 101% by weight, 15 to 100% by weight, 15 to 99% by weight, 15 to 98% by weight, 15 to 97% by weight, 15 to 96% by weight, 15 to 95% by weight, 15 to 94% by weight, 15 to 93% by weight, 16 to 140% by weight, 16 to 139% by weight, 16 to 138% by weight, 16 to 137% by weight, 16 to 136% by weight, 16 to 135% by weight, 16 to 134% by weight, 16 to 133% by weight, 16 to 132% by weight, 16 to 131% by weight, 16 to 130% by weight, 16 to 129% by weight, 16 to 128% by weight, 16 to 127% by weight, 16 to 126% by weight, 16 to 125% by weight, 16 to 124% by weight, 16 to 123% by weight, 16 to 122% by weight, 16 to 121% by weight, 16 to 120% by weight, 16 to 119% by weight, 16 to 118% by weight, 16 to 117% by weight, 16 to 116% by weight, 16 to 115% by weight, 16 to 114% by weight, 16 to 113% by weight, 16 to 112% by weight, 16 to 111% by weight, 16 to 110% by weight, 16 to 109% by weight, 16 to 108% by weight, 16 to 107% by weight, 16 to 106% by weight, 16 to 105% by weight, 16 to 104% by weight, 16 to 103% by weight, 16 to 102% by weight, 16 to 101% by weight, 16 to 100% by weight, 16 to 99% by weight, 16 to 98% by weight, 16 to 97% by weight, 16 to 96% by weight, 16 to 95% by weight, 16 to 94% by weight, 16 to 93% by weight, 17 to 140% by weight, 17 to 139% by weight, 17 to 138% by weight, 17 to 137% by weight, 17 to 136% by weight, 17 to 135% by weight, 17 to 134% by weight, 17 to 133% by weight, 17 to 132% by weight, 17 to 131% by weight, 17 to 130% by weight, 17 to 129% by weight, 17 to 128% by weight, 17 to 127% by weight, 17 to 126% by weight, 17 to 125% by weight, 17 to 124% by weight, 17 to 123% by weight, 17 to 122% by weight, 17 to 121% by weight, 17 to 120% by weight, 17 to 119% by weight, 17 to 118% by weight, 17 to 117% by weight, 17 to 116% by weight, 17 to 115% by weight, 17 to 114% by weight, 17 to 113% by weight, 17 to 112% by weight, 17 to 111% by weight, 17 to 110% by weight, 17 to 109% by weight, 17 to 108% by weight, 17 to 107% by weight, 17 to 106% by weight, 17 to 105% by weight, 17 to 104% by weight, 17 to 103% by weight, 17 to 102% by weight, 17 to 101% by weight, 17 to 100% by weight, 17 to 99% by weight, 17 to 98% by weight, 17 to 97% by weight, 17 to 96% by weight, 17 to 95% by weight, 17 to 94% by weight, 17 to 93% by weight, 18 to 140% by weight, 18 to 139% by weight, 18 to 138% by weight, 18 to 137% by weight, 18 to 136% by weight, 18 to 135% by weight, 18 to 134% by weight, 18 to 133% by weight, 18 to 132% by weight, 18 to 131% by weight, 18 to 130% by weight, 18 to 129% by weight, 18 to 128% by weight, 18 to 127% by weight, 18 to 126% by weight, 18 to 125% by weight, 18 to 124% by weight, 18 to 123% by weight, 18 to 122% by weight, 18 to 121% by weight, 18 to 120% by weight, 18 to 119% by weight, 18 to 118% by weight, 18 to 117% by weight, 18 to 116% by weight, 18 to 115% by weight, 18 to 114% by weight, 18 to 113% by weight, 18 to 112% by weight, 18 to 111% by weight, 18 to 110% by weight, 18 to 109% by weight, 18 to 108% by weight, 18 to 107% by weight, 18 to 106% by weight, 18 to 105% by weight, 18 to 104% by weight, 18 to 103% by weight, 18 to 102% by weight, 18 to 101% by weight, 18 to 100% by weight, 18 to 99% by weight, 18 to 98% by weight, 18 to 97% by weight, 18 to 96% by weight, 18 to 95% by weight, 18 to 94% by weight or 18 to 93% by weight, compared to a therapeutically effective amount of the patient in case of its monotherapy.

In one embodiment, the therapeutically effective amount of lamotrigine may be increased to compensate about 10 to 60%, 10 to 59%, 10 to 58%, 10 to 57%, 10 to 56%, 10 to 55%, 10 to 54%, 10 to 53%, 10 to 52%, 11 to 60%, 11 to 59%, 11 to 58%, 11 to 57%, 11 to 56%, 11 to 55%, 11 to 54%, 11 to 53%, 11 to 52%, 12 to 60%, 12 to 59%, 12 to 58%, 12 to 57%, 12 to 56%, 12 to 55%, 12 to 54%, 12 to 53%, 12 to 52%, 13 to 60%, 13 to 59%, 13 to 58%, 13 to 57%, 13 to 56%, 13 to 55%, 13 to 54%, 13 to 53%, 13 to 52%, 14 to 60%, 14 to 59%, 14 to 58%, 14 to 57%, 14 to 56%, 14 to 55%, 14 to 54%, 14 to 53%, 14 to 52%, 15 to 60%, 15 to 59%, 15 to 58%, 15 to 57%, 15 to 56%, 15 to 55%, 15 to 54%, 15 to 53%, 15 to 52%, 16 to 60%, 16 to 59%, 16 to 58%, 16 to 57%, 16 to 56%, 16 to 55%, 16 to 54%, 16 to 53%, 16 to 52%, 17 to 60%, 17 to 59%, 17 to 58%, 17 to 57%, 17 to 56%, 17 to 55%, 17 to 54%, 17 to 53%, 17 to 52%, 18 to 60%, 18 to 59%, 18 to 58%, 18 to 57%, 18 to 56%, 18 to 55%, 18 to 54%, 18 to 53%, 18 to 52%, 19 to 60%, 19 to 59%, 19 to 58%, 19 to 57%, 19 to 56%, 19 to 55%, 19 to 54%, 19 to 53%, 19 to 52%, 20 to 60%, 20 to 59%, 20 to 58%, 20 to 57%, 20 to 56%, 20 to 55%, 20 to 54%, 20 to 53%, 20 to 52%, 21 to 60%, 21 to 59%, 21 to 58%, 21 to 57%, 21 to 56%, 21 to 55%, 21 to 54%, 21 to 53% or 21 to 52% reduction in AUC of lamotrigine obtained after the co-administration to the level of AUC obtained after the administration of lamotrigine to the patient without cenobamate.

To increase the therapeutically effective amount of lamotrigine to the level of AUC obtained after the administration of lamotrigine to the patient without cenobamate as described above, the therapeutic effective amount of lamotrigine needs to be increased as described above. The correlation between the AUC of lamotrigine and its therapeutically effective amount is referenced in the article [FABAD J. Pharm. Sci., 31, 163-179 (2006)] and information can be obtained therefrom about how much the therapeutically effective amount of lamotrigine needs to be increased to achieve the targeting AUC.

In one embodiment, the therapeutically effective amount of lamotrigine in case of its monotherapy may be from about 100 mg/day to about 500 mg/day. In one embodiment, the therapeutically effective amount of lamotrigine may be about 100 mg/day or about 200 mg/day. In one embodiment, in patients in which lamotrigine is administered with the therapeutically effective amount of about 100 mg/day to about 200 mg/day, when co-administered with cenobamate, the therapeutically effective amount of lamotrigine may be increased by from about 7.1 mg/day to about 280.1 mg/day. In one embodiment, in patients in which lamotrigine is administered with the therapeutically effective amount of about 100 mg/day, the therapeutically effective amount of lamotrigine may be increased by from about 7.1 mg/day to about 130.1 mg/day. In one embodiment, in patients in which lamotrigine is administered with the therapeutically effective amount of about 200 mg/day, the therapeutically effective amount of lamotrigine may be increased by from about 19.0 mg/day to about 280.1 mg/day. In one embodiment, in patients in which lamotrigine is administered with the therapeutically effective amount of about 100 mg/day, the therapeutically effective amount of lamotrigine may be increased by from about 18.5 mg/day to about 85.2 mg/day. In one embodiment, in patients in which lamotrigine may be administered with the therapeutically effective amount of about 200 mg/day, the therapeutically effective amount of lamotrigine may be increased by from about 43.5 mg/day to about 185.1 mg/day. In one embodiment, in patients in which lamotrigine is administered with the therapeutically effective amount of about 100 mg/day, when co-administered with cenobamate, the therapeutically effective amount of lamotrigine may be from about 107.1 mg/day to about 230.1 mg/day. In one embodiment, in patients in which lamotrigine is administered with the therapeutically effective amount of about 200 mg/day, when co-administered with cenobamate, the therapeutically effective amount of lamotrigine may be from about 219.0 mg/day to about 480.1 mg/day. In one embodiment, the maximum dose of lamotrigine is about 500 mg/day.

In one embodiment, the antiepileptic drug may be phenobarbital.

In one embodiment, a therapeutically effective amount of phenobarbital in case of its monotherapy may be about from about 60 mg/day to about 180 mg/day.

In one embodiment, the therapeutically effective amount of phenobarbital may be decreased by about 20 to 50% by weight, 20 to 49% by weight, 20 to 48% by weight, 20 to 47% by weight, 20 to 46% by weight, 20 to 45% by weight, 21 to 50% by weight, 21 to 49% by weight, 21 to 48% by weight, 21 to 47% by weight, 21 to 46% by weight, 21 to 45% by weight, 22 to 50% by weight, 22 to 49% by weight, 22 to 48% by weight, 22 to 47% by weight, 22 to 46% by weight, 22 to 45% by weight, 23 to 50% by weight, 23 to 49% by weight, 23 to 48% by weight, 23 to 47% by weight, 23 to 46% by weight, 23 to 45% by weight, 24 to 50% by weight, 24 to 49% by weight, 24 to 48% by weight, 24 to 47% by weight, 24 to 46% by weight, 24 to 45% by weight, 25 to 50% by weight, 25 to 49% by weight, 25 to 48% by weight, 25 to 47% by weight, 25 to 46% by weight or 25 to 45% by weight, compared to a therapeutically effective amount of the patient in case of its monotherapy.

In one embodiment, the therapeutically effective amount of phenobarbital may be decreased to adjust about 20 to 50%, 20 to 49%, 20 to 48%, 20 to 47%, 20 to 46%, 20 to 45%, 21 to 50%, 21 to 49%, 21 to 48%, 21 to 47%, 21 to 46%, 21 to 45%, 22 to 50%, 22 to 49%, 22 to 48%, 22 to 47%, 22 to 46%, 22 to 45%, 23 to 50%, 23 to 49%, 23 to 48%, 23 to 47%, 23 to 46%, 23 to 45%, 24 to 50%, 24 to 49%, 24 to 48%, 24 to 47%, 24 to 46%, 24 to 45%, 25 to 50%, 25 to 49%, 25 to 48%, 25 to 47%, 25 to 46% or 25 to 45% increase in AUC of phenobarbital obtained after the co-administration to the level of AUC obtained after the administration of phenobarbital to the patient without cenobamate.

In one embodiment, the antiepileptic drug may be phenytoin.

In one embodiment, the therapeutically effective amount of phenytoin may be decreased by about 7 to 55% by weight, 7 to 54% by weight, 7 to 53% by weight, 7 to 52% by weight, 7 to 51% by weight, 7 to 50% by weight, 7 to 49% by weight, 7 to 48% by weight, 7 to 47% by weight, 7 to 46% by weight, 7 to 45% by weight, 7 to 44% by weight, 7 to 43% by weight, 7 to 42% by weight, 7 to 41% by weight, 7 to 40% by weight, 8 to 55% by weight, 8 to 54% by weight, 8 to 53% by weight, 8 to 52% by weight, 8 to 51% by weight, 8 to 50% by weight, 8 to 49% by weight, 8 to 48% by weight, 8 to 47% by weight, 8 to 46% by weight, 8 to 45% by weight, 8 to 44% by weight, 8 to 43% by weight, 8 to 42% by weight, 8 to 41% by weight, 8 to 40% by weight, 9 to 55% by weight, 9 to 54% by weight, 9 to 53% by weight, 9 to 52% by weight, 9 to 51% by weight, 9 to 50% by weight, 9 to 49% by weight, 9 to 48% by weight, 9 to 47% by weight, 9 to 46% by weight, 9 to 45% by weight, 9 to 44% by weight, 9 to 43% by weight, 9 to 42% by weight, 9 to 41% by weight, 9 to 40% by weight, 10 to 55% by weight, 10 to 54% by weight, 10 to 53% by weight, 10 to 52% by weight, 10 to 51% by weight, 10 to 50% by weight, 10 to 49% by weight, 10 to 48% by weight, 10 to 47% by weight, 10 to 46% by weight, 10 to 45% by weight, 10 to 44% by weight, 10 to 43% by weight, 10 to 42% by weight, 10 to 41% by weight or 10 to 40% by weight, compared to a therapeutically effective amount of the patient in case of its monotherapy.

In one embodiment, the therapeutically effective amount of phenytoin may be decreased to adjust about 10 to 100%, 10 to 99%, 10 to 98%, 10 to 97%, 10 to 96%, 10 to 95%, 10 to 94%, 10 to 93%, 10 to 92%, 10 to 91%, 10 to 90%, 10 to 89%, 10 to 88%, 10 to 87%, 10 to 86%, 10 to 85%, 10 to 84%, 10 to 83%, 10 to 82%, 10 to 81%, 10 to 80%, 10 to 79%, 10 to 78%, 10 to 77%, 10 to 76%, 10 to 75%, 10 to 74%, 10 to 73%, 10 to 72%, 10 to 71%, 10 to 70%, 10 to 69%, 10 to 68%, 10 to 67%, 10 to 66%, 10 to 65%, 10 to 64%, 10 to 63%, 10 to 62%, 10 to 61% or 10 to 60% increase in AUC of phenytoin obtained after the co-administration to the level of AUC obtained after the administration of phenytoin to the patient without cenobamate.

To decrease the therapeutically effective amount of phenytoin to have the level of AUC obtained after the administration of phenytoin to the patient without cenobamate as described above, therapeutically effective amount of phenytoin needs to be decreased as described above. The correlation between the AUC of phenytoin and its therapeutically effective amount is referenced in the article [J Med Assoc Thai Vol. 90, No. 9 (2007)] and information can be obtained therefrom about how much the therapeutically effective amount of phenytoin needs to be decreased to achieve the targeting AUC.

In one embodiment, the therapeutically effective amount of phenytoin in case of its monotherapy may be from about 300 mg/day to about 600 mg/day. In one embodiment, the therapeutically effective amount of phenytoin may be about 300 mg/day or about 600 mg/day. In one embodiment, in patients in which phenytoin is administered with the therapeutically effective amount of about 300 mg/day to about 600 mg/day, when co-administered with cenobamate, the therapeutically effective amount of phenytoin may be decreased by from about 32 mg/day to about 291.8 mg/day. In one embodiment, in patients in which phenytoin is administered with the therapeutically effective amount of about 300 mg/day, the therapeutically effective amount of phenytoin may be decreased by from about 32 mg/day to about 145.9 mg/day. In one embodiment, in patients in which phenytoin is administered with the therapeutically effective amount of about 300 mg/day, the therapeutically effective amount of phenytoin may be decreased by from about 32 mg/day to about 116.7 mg/day. In one embodiment, in patients in which phenytoin is administered with the therapeutically effective amount of about 600 mg/day, the therapeutically effective amount of phenytoin may be decreased by from about 64 mg/day to about 291.8 mg/day. In one embodiment, in patients in which phenytoin is administered with the therapeutically effective amount of about 600 mg/day, when co-administered with cenobamate, the therapeutically effective amount of phenytoin may be from about 154.1 mg/day to about 268 mg/day. In one embodiment, in patients in which phenytoin is administered with the therapeutically effective amount of about 600 mg/day, when co-administered with cenobamate, the therapeutically effective amount of phenytoin may be from about 308.2 mg/day to about 536 mg/day.

Another embodiment of the present disclosure is a method for treating a patient who is suffering from epilepsy with co-administering a therapeutically effective amount of (i) cenobamate or a pharmaceutically acceptable salt thereof and (ii) phenytoin, said method comprising:

increasing the therapeutically effective amount of cenobamate to compensate about 20% to about 40% reduction in AUC of cenobamate obtained after the co-administration to the level of AUC obtained after the administration of cenobamate to the patient without phenytoin.

In one embodiment, cenobamate or a pharmaceutically acceptable salt thereof may be administered to the patient with the following titration method:

(1) administering cenobamate to the patient about 12.5 mg once daily for about two weeks;
(2) then administering cenobamate to the patient about 25 mg once daily for two weeks;
(3) then administering cenobamate to the patient about 50 mg once daily for about two weeks; and
(4) then increasing the dose in about bi-weekly increments by no more than about 50 mg once daily to a therapeutically effective amount.

In one embodiment, the therapeutically effective amount of cenobamate may be achieved by the following titration method:

(1) administering cenobamate to the patient about 50 mg once daily for about two weeks; and
(2) then increasing the dose in about bi-weekly increments by about 50 mg once daily to about 200 mg/day once daily, wherein cenobamate is administered for about 6 weeks and the therapeutically effective amount of cenobamate is about 200 mg/day.

In one embodiment, the therapeutically effective amount of cenobamate may be achieved by the following titration method:

(1) administering cenobamate to the patient about 50 mg once daily which is increased with 50 mg once daily per week to about 100 mg/day;

(2) optionally increasing the dose in about weekly increments by about 50 mg once daily per week to about 200 mg/day; and (3) optionally increasing the dose in about weekly increments by about 100 mg/day per week to about 400 mg/day, wherein cenobamate is administered for about 2 weeks, 4 weeks, or 6 weeks depending on therapeutically effective amount of cenobamate which is required and the therapeutically effective amount of cenobamate is about 100 mg/day, about 200 mg/day or about 400 mg/day.

In one embodiment, the therapeutically effective amount of cenobamate or a pharmaceutically acceptable salt thereof in case of its monotherapy may be ranging from about 100 mg/day to about 400 mg/day.

In one embodiment, the therapeutically effective amount of cenobamate may be increased by about 50% by weight, compared to its therapeutically effective amount of the patient in case of its monotherapy.

In one embodiment, the therapeutically effective amount of cenobamate is increased to compensate about 20 to 40%, 20 to 39%, 20 to 38%, 20 to 37%, 20 to 36%, 20 to 35%, 21 to 40%, 21 to 39%, 21 to 38%, 21 to 37%, 21 to 36%, 21 to 35%, 22 to 40%, 22 to 39%, 22 to 38%, 22 to 37%, 22 to 36%, 22 to 35%, 23 to 40%, 23 to 39%, 23 to 38%, 23 to 37%, 23 to 36%, 23 to 35%, 24 to 40%, 24 to 39%, 24 to 38%, 24 to 37%, 24 to 36%, 24 to 35%, 25 to 40%, 25 to 39%, 25 to 38%, 25 to 37%, 25 to 36% or 25 to 35% reduction in AUC of cenobamate obtained after the co-administration to the level of AUC obtained after the administration of cenobamate to the patient without phenytoin.

Still another embodiment of the present disclosure is a pharmaceutical composition for the prevention or treatment of epilepsy, comprising a therapeutically effective amount of (i) cenobamate or a pharmaceutically acceptable salt thereof and (ii) one or more antiepileptic drugs, wherein the therapeutically effective amount of the antiepileptic drug is modified to adjust AUC of the antiepileptic drug obtained after the co-administration having at least 5% difference to the level of AUC obtained after the administration of antiepileptic drug to the patient without cenobamate or a pharmaceutically acceptable salt thereof.

Still another embodiment of the present disclosure is a pharmaceutical composition for the prevention or treatment of epilepsy, comprising a therapeutically effective amount of (i) cenobamate or a pharmaceutically acceptable salt thereof and (ii) phenytoin, wherein the therapeutically effective amount of cenobamate is increased to compensate about 20% to about 40% reduction in AUC of cenobamate obtained after the co-administration to the level of AUC obtained after the administration of cenobamate to the patient without phenytoin.

Still another embodiment of the present disclosure is use of a pharmaceutical composition comprising a therapeutically effective amount of (i) cenobamate or a pharmaceutically acceptable salt thereof and (ii) one or more antiepileptic drugs in the prevention or treatment of epilepsy, wherein the therapeutically effective amount of the antiepileptic drug is modified to adjust AUC of the antiepileptic drug obtained after the co-administration having at least 5% difference to the level of AUC obtained after the administration of antiepileptic drug to the patient without cenobamate or a pharmaceutically acceptable salt thereof.

Still another embodiment of the present disclosure is use of a pharmaceutical composition comprising a therapeutically effective amount of (i) cenobamate or a pharmaceutically acceptable salt thereof and (ii) phenytoin in the prevention or treatment of epilepsy, wherein the therapeutically effective amount of cenobamate is increased to compensate about 20% to about 40% reduction in AUC of cenobamate obtained after the co-administration to the level of AUC obtained after the administration of cenobamate to the patient without phenytoin.

In one embodiment, the pharmaceutical composition may be administered by a conventional method used for administration of a therapeutic agent, such as oral administration.

In one embodiment, examples of the pharmaceutically acceptable salts of cenobamate include, but are not limited to, acetate, benzenesulfonate, benzoate, bitartrate, calcium acetate, camsylate, carbonate, citrate, edetate, edisylate, estolate, esylate, fumarate, gluceptate, gluconate, glutamate, glycoloyl arsanilate, hexylresorcinate hydrabamine, hydrobromide, hydrochloride, hydrogencarbonate, hydroxynaphtoate, iodide, isethionate, lactate, lactobionate, malate, maleate, mandelate, mesylate, methylnitrate, methylsulfate, mucate, napsylate, nitrate, pamoate (embonate), pantothenate, phosphate/diphosphate, polygalacturonate, salicylate, stearate, subacetate, succinate or hemi-succinate, sulfate or hemi-sulfate, tannate, tartrate, oxalate or hemi-tartrate, teoclate, triethiodide, benzathine, chloroprocaine, choline, diethanolamine, diethyleneamine, meglumine, procaine, aluminum, ammonium, tetramethylammonium, calcium, lithium, magnesium, potassium, sodium and zinc.

In one embodiment, the pharmaceutical composition may be administered orally. The composition can be administered by any device capable of transferring the active substance to a target cell.

In one embodiment, the pharmaceutical composition may be formulated using a pharmaceutically acceptable carrier and/or excipient according to a method that a person having ordinary skill in the art could easily carry out, thereby to be prepared in a unit dose form or to be contained in a multi-dose container. The above formulation may be a solution in oil or an aqueous medium, a suspension or an emulsion (emulsified solution), an extract, a powder, granules, a tablet, or a capsule, and may further include a dispersing or stabilizing agent. The pharmaceutical composition may also be prepared for mammalian administration, more preferably for human administration.

Pharmaceutically acceptable carriers may be solid or liquid, and may be one or more selected from fillers, antioxidants, buffers, bacteriostats, dispersants, adsorbents, surfactants, binders, preservatives, disintegrants, sweeteners, flavors, glidants, release-controlling agents, wetting agents, stabilizers, suspending agents, and lubricants. In addition, the pharmaceutically acceptable carriers may be selected from saline, sterile water, Ringer's solution, buffered saline, dextrose solution, maltodextrin solution, glycerol, ethanol and mixtures thereof.

In one embodiment, suitable fillers include, but are not limited to, sugar (e.g., dextrose, sucrose, maltose and lactose), starch (e.g., corn starch), sugar alcohol (e.g., mannitol, sorbitol, maltitol, erythritol and xylitol), starch hydrolysate (e.g., dextrin and maltodextrin), cellulose or cellulose derivative (e.g., microcrystalline cellulose) or mixtures thereof.

In one embodiment, suitable binders include, but are not limited to, povidone, copovidone, methylcellulose, hydroxypropylmethylcellulose, hydroxypropylcellulose, hydroxyethylcellulose, gelatin, gum, sucrose, starch or mixtures thereof.

In one embodiment, suitable preservatives include, but are not limited to, benzoic acid, sodium benzoate, benzyl alcohol, butylated hydroxyanisole, butylated hydroxytoluene, chlorbutol, gallate, hydroxybenzoate, EDTA or mixtures thereof.

In one embodiment, suitable disintegrants include, but are not limited to, sodium starch glycolate, cross-linked polyvinylpyrrolidone, cross-linked carboxymethylcellulose, starch, microcrystalline cellulose or mixtures thereof.

In one embodiment, suitable sweeteners include, but are not limited to, sucralose, saccharin, sodium saccharin, potassium saccharin, calcium saccharin, acesulfame potassium or sodium cyclamate, mannitol, fructose, sucrose, maltose or mixtures thereof.

In one embodiment, suitable glidants include, but are not limited to, silica, colloidal silicon dioxide, talc and the like.

In one embodiment, suitable lubricants include, but are not limited to, long chain fatty acids and salts thereof, such as magnesium stearate and stearic acid, talc, glyceride wax or mixtures thereof.

Effect of the Invention

The present disclosure provides an effective combination therapy of cenobamate and other antiepileptic drugs.

DETAILED DESCRIPTION

Figure 1:
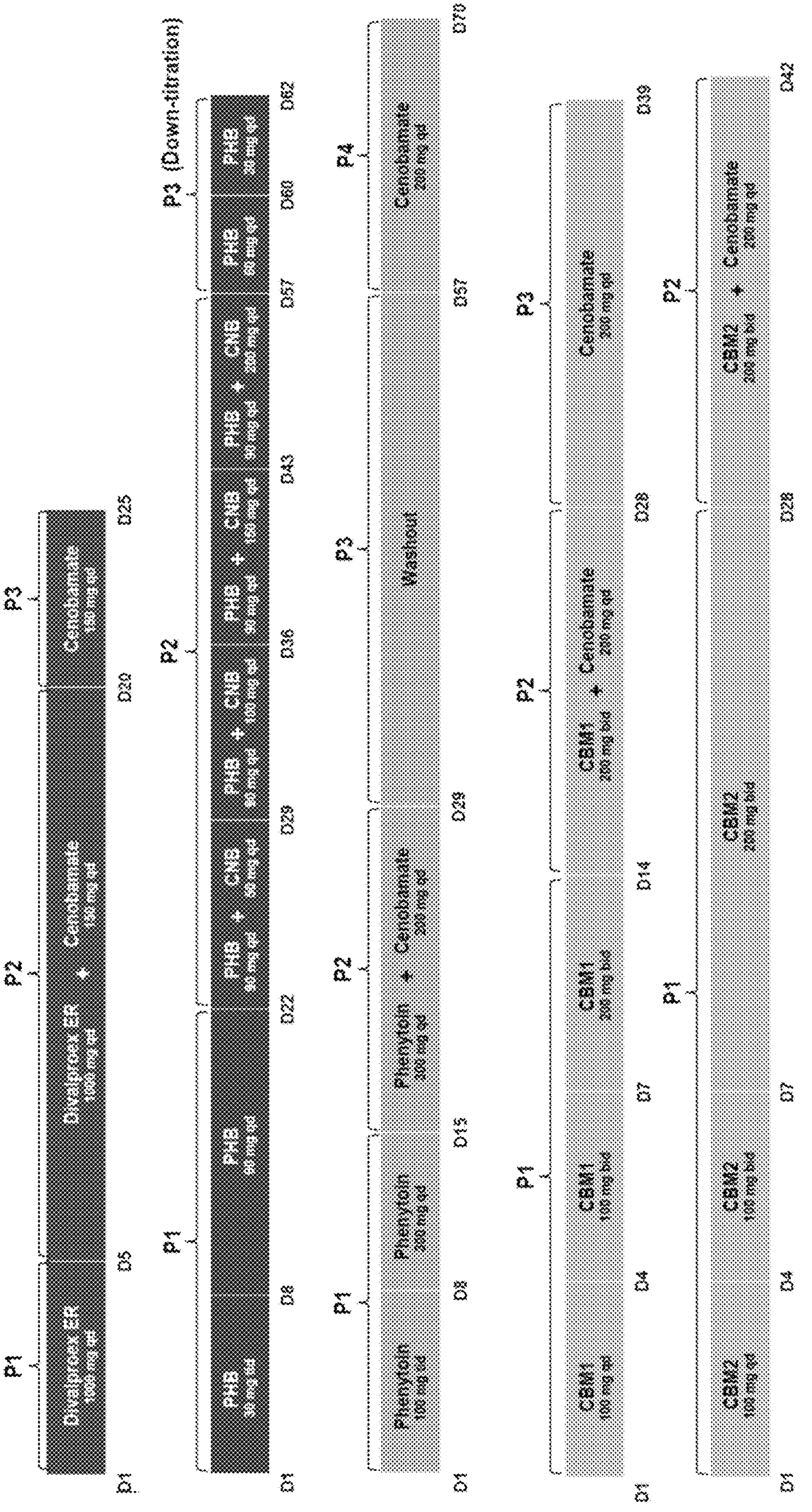
FIG. 1 shows study designs for pharmacokinetic drug interaction study (CBM1: carbamazepine (Tegretol), CBM2: carbamazepine (Carbatrol), CNB: cenobamate, D: day, P: period, PHB: phenobarbital).

Hereinafter, the present disclosure will be explained in more detail with examples.

Example 1

This study was carried out to assess the effect of cenobamate on the disposition of four AEDs (divalproex sodium, phenobarbital, phenytoin and carbamazepine) and the effect of four AEDs on the disposition of cenobamate. The details are described below.

Study Designs

Five open-label, multiple dose, multiple period, 1 sequence, PK drug-interaction studies were conducted examining co-administration of cenobamate and each of the above-mentioned AEDs. Specifically, five studies were conducted, as follows:

Study 1—Divalproex Sodium

This is an open-label, multiple-dose, 1 sequence, 3 period pharmacokinetic drug interaction study between cenobamate and divalproex in normal volunteer subjects. Sixteen subjects were enrolled. All subjects were scheduled to undergo 3 treatment periods as a 1 sequence design:

Period 1 (Days 1 to 5): Single oral daily administration of 1000 mg divalproex (Treatment A).

Period 2 (Days 6 to 19): Co-administration of single oral daily administration of 1000 mg divalproex and 150 mg cenobamate (Treatments A and B).

Period 3 (Days 20 to 25): Single oral daily administration of 150 mg cenobamate (Treatment B). (Number of Subjects Planned: 16 Enrolled: 16 Analyzed: 16)

Study 2—Phenobarbital

This is an open-label, 1-arm, 2-treatment study. Sixteen (16) healthy, adult, non-tobacco using, male and female subjects were enrolled. Screening of subjects occurred within 28 days prior to the first dose. A total of 16 subjects were enrolled in the study, and 14 subjects completed the study. The PK dataset therefore included 16 subjects for phenobarbital alone and 14 subjects for the combination treatment. There were 16 subjects included in the safety analyses.

Treatment A subjects received 30 mg phenobarbital TID on Days 1 to 7, followed by 90 mg phenobarbital QD in the morning on Days 8 to 21. All study drugs were administered orally with approximately 240 mL of water.

Treatment B subjects received 90 mg phenobarbital QD in the morning from Days 22 to 56 co-administered with 50 mg cenobamate QD on Days 22 to 28, 100 mg cenobamate QD on Days 29 to 35, 150 mg cenobamate QD on Days 36 to 42, and 200 mg cenobamate QD on Days 43 to 56. All study drugs were administered orally with approximately 240 mL of water. The study duration was approximately 13 weeks from screening to end-of-study procedures. There was approximately 17 weeks from screening to attempted follow-up phone call. There was no washout.

Study 3—Phenytoin

This is an open-label, multiple-dose, 1-sequence, 4-period pharmacokinetic (PK) drug interaction study between cenobamate and phenytoin in healthy volunteer subjects. Sixteen (16) subjects were enrolled. They were to be confined to the testing facility for the duration of Periods 1, 2, and 4 of the study. Subjects were screened from Days −21 to −2. Subsequently, all subjects were to undergo the following 4 treatment periods as a 1 sequence design:

Period 1 (Days 1 to 14): Phenytoin alone (Treatment A). Dosing schedule: Days 1-7: 100 mg 3 times daily (TID); Days 8-14: 300 mg once daily (QD) at 8 pm.

Period 2 (Days 15 to 28): Phenytoin and cenobamate (Treatment B). Phenytoin 300 mg QD at 8 pm and cenobamate 200 mg QD at 8 pm.

Period 3 (Days 29 to 56): Washout.

Period 4 (Days 57 to 70): cenobamate alone (Treatment C). 200 mg QD at 8 pm.

Blood samples were obtained prior to and following dosing at selected times through 24 hours postdose on selected days (Days 14, 28, and 70). Plasma samples were analyzed for phenytoin and cenobamate concentrations using validated analytical methods. Appropriate PK parameters were calculated for each treatment using non-compartmental methods. A total of 16 subjects entered the study and received study treatment. Nine (9) subjects completed 4 periods of the study. Seven (7) subjects discontinued early. All 16 subjects were included in the PK analyses for Period 1 (Treatment A), while 10 subjects were included for Period 2 (Treatment B) and 9 subjects were included for Period 3 (Treatment C). All 16 subjects were included in the safety analyses.

Study 4—Carbamazepine 1

This is an open-label, multiple-dose, 1-sequence, 3-period pharmacokinetic drug interaction study between cenobamate and carbamazepine in normal volunteer subjects. Sixteen subjects were enrolled. All subjects were scheduled to undergo 3 treatment periods as a 1-sequence design:

Period 1 (Days 1 to 14): Once daily (Days 1-3) followed by twice daily (Days 4-14) oral administration of increasing doses of carbamazepine (carbamazepine 100 mg/day to 400 mg/day) (Treatment A).

Period 2 (Days 15 to 28): Twice daily oral administration of carbamazepine 200 mg and once daily oral administration of cenobamate 200 mg (Treatments A and B).

Period 3 (Days 29 to 39): Single daily oral administration of cenobamate 200 mg (Treatment B).

Number of Subjects Planned: 16 Enrolled: 16 Analyzed: 15

Study 5—Carbamazepine 2

This is an open-label, multiple-dose, one-sequence, two-period pharmacokinetic drug interaction study between cenobamate and carbamazepine in normal volunteer subjects. Sixteen subjects were enrolled. All subjects were scheduled to undergo two treatment periods as a one-sequence design:

Period 1 (Days 1 to 28): Once daily (Days 1-3) followed by twice daily (Days 4-28) oral administration of increasing doses of carbamazepine (carbamazepine 100 mg/day to 400 mg/day) (Treatment A). The subjects were not confined to the clinic during this period except for the first two days and around Days 14 and 28, when pharmacokinetic blood samples were drawn.

Period 2 (Days 29 to 42): Twice daily oral administration of carbamazepine 200 mg and once daily oral administration of cenobamate 200 mg (Treatments A and B). The subjects were confined during this period.

Number of Subjects Planned: 16 Enrolled: 16 Analyzed: 15

The study designs of 5 (five) studies above are summarized in FIG. 1.

After collecting data from those studies, they are analyzed, as follows.

Endpoints and Measures

Primary and Secondary Endpoints

PK parameters: AUC and Cmax for cenobamate and each AED

Safety and tolerability assessed through adverse events (AEs) by system organ class (SOC) and laboratory evaluations Methods Cenobamate and AED plasma concentrations were measured using validated bioanalytical methods PK parameters were calculated using Phoenix WinNonlin v5.2 or v6.3 and SAS v9.1 or v9.3

Statistical analyses were performed using SAS v9.1 or v9.1.3 to estimate the differences between treatments on transformed values for Cmax and AUC Ratios of the geometric means (based on LS means) of Cmax and AUC were calculated and expressed as a percentage relative to the reference treatment (either the add-on AED alone or cenobamate alone)—The 90% CIs about the ratios of the geometric means were determined and the following comparisons were performed:

[A+B] vs A alone for add-on AED

[A+B] vs B alone for cenobamate

A lack of significant differences in PK exposure parameters across treatment periods (no significant drug interaction) was determined if the 90% confidence intervals were within the accepted limits of 80% and 125%.

Figure 2:
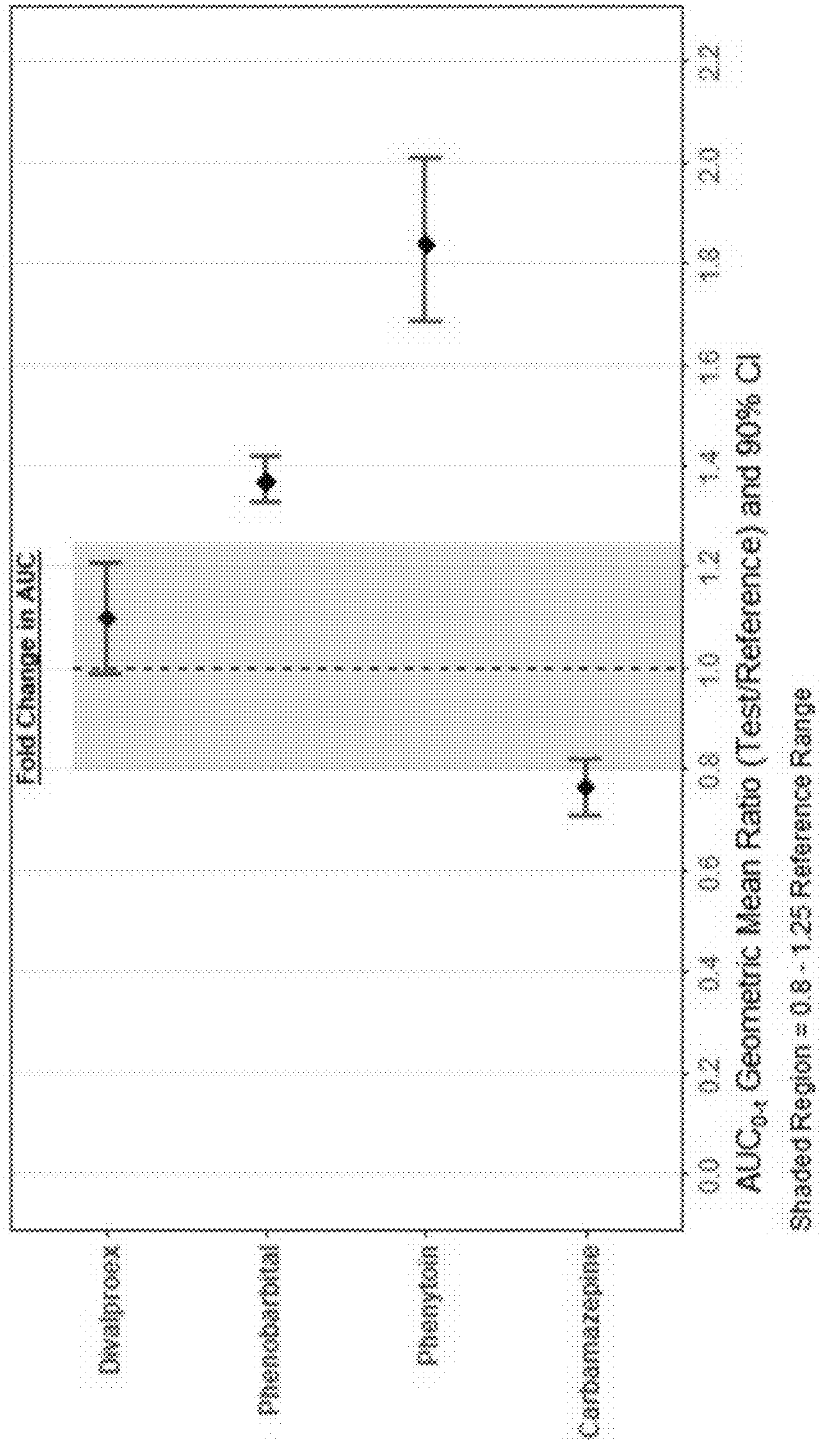
FIG. 2 is a graph showing the effect of cenobamate on the systemic exposure (AUC) of each antiepileptic drug.
Figure 3:
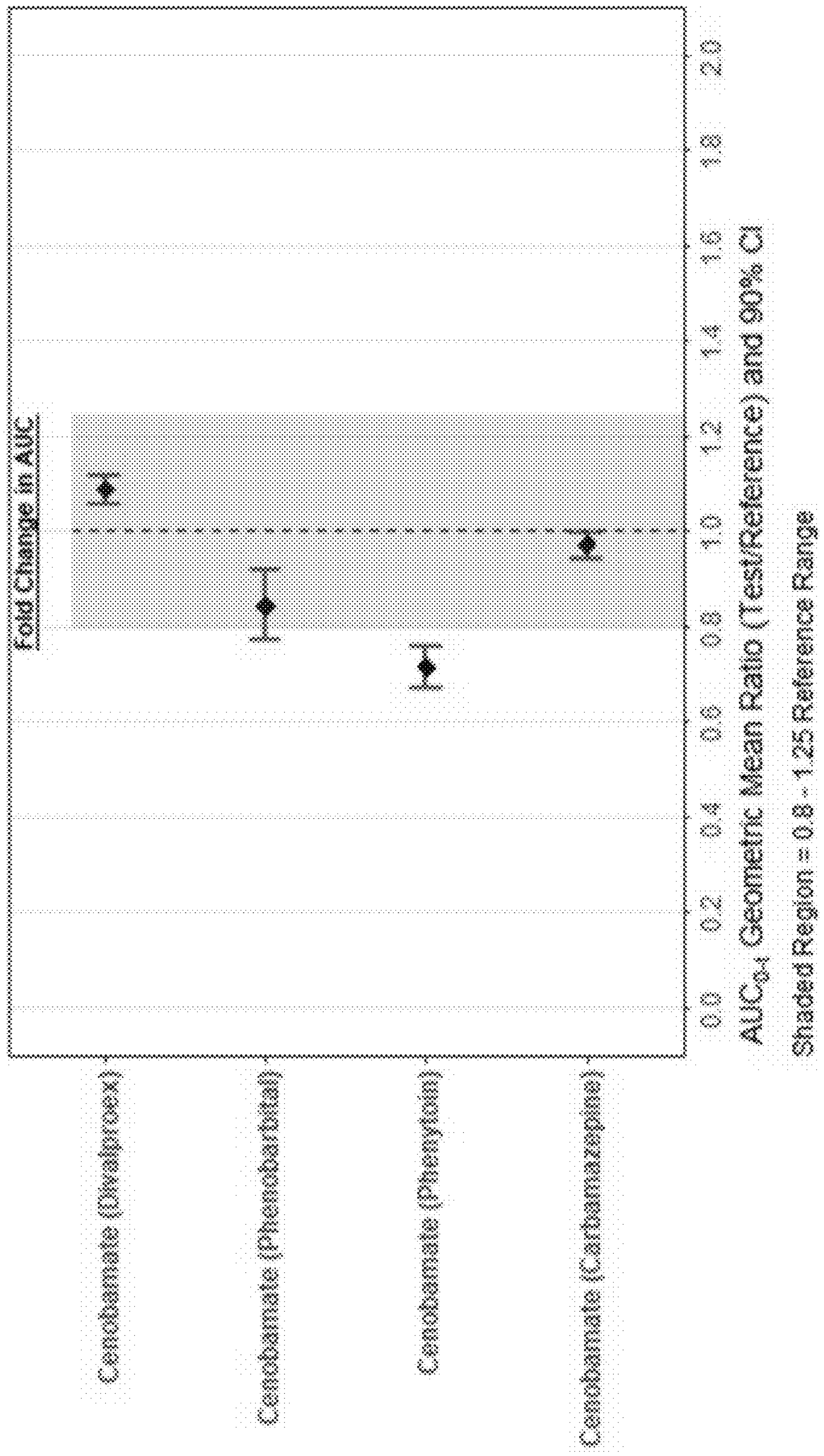
FIG. 3 is a graph showing the effect of each antiepileptic drug on the systemic exposure (AUC) of cenobamate.

Combination therapy with cenobamate resulted in increased plasma Cmax and AUC of phenobarbital and phenytoin and decreased exposure for carbamazepine (FIG. 2), and thus, dose adjustment of phenobarbital, phenytoin and carbamazepine is necessary when these drugs are used in combination with cenobamate. Further, combination therapy with phenytion and cenobamate resulted in decreased plasma Cmax and AUC for cenobamate (FIG. 3), and thus, dose adjustment of cenobamate is necessary when cenobamate is used in combination with phenytoin.

Example 2

This study was carried out to make an assessment of the extent to which the adjunctive treatment with cenobamate may affect the recommended dosing of other AEDs. Population pharmacokinetics (PopPK) models describing how cenobamate exposure affects that of other commonly used AEDs (i.e., carbamazepine, lamotrigine, levetiracetam, oxcarbazepine, phenytoin and valproic acid) when given as adjunct therapy.

Therapeutically effective amount for AEDs are different depending on the condition of subjects participated in the study. For carbamazepine, therapeutically effective amount was about 800 mg/day to about 1,200 mg/day for adults and children over 12 years of age. For lamotrigine, therapeutically effective amount was about 100 mg/day to about 500 mg/day, preferably about 100 mg/day to 200 mg/day, for adults and children over 12 years of age. For levetiracetam, therapeutically effective amount was about 3,000 mg/day for adults and children over 12 years of age. For phenytoin, therapeutically effective amount was about 300 mg/day to about 600 mg/day for adults. For valproic acid, therapeutically effective amount was about 60 mg/kg/day for adults.

1. General Data Assembly Process

PopPk datasets were constructed from clinical databases for Cenobamate Study 1, Cenobamate Study 2 and Cenobamate Study 3. The dosing, exposure, covariate and AED concentration data were merged by subject, date, and time; formatted for PopPK analysis and saved in ASCII format using R software (Version 3.2.2, Comprehensive R Network, cran.r-project.org). All data programs were documented and archived in a locked on-line repository in order to maintain an audit trail. A quality control (QC) check of the data management procedure was conducted according to qPharmetra standard operating procedures (SOPs).

2. Analysis Data

Results from Cenobamate Study 1, Cenobamate Study 2 and Cenobamate Study 3 were included in the analyses. Each study is described in more detail in the subsequent sections.

(1) Efficacy and Safety Study—Cenobamate Study 1

This is a multicenter, double-blind, randomized, adjunctive placebo-controlled trial with an open-label extension phase to evaluate the efficacy and safety of cenobamate in subjects with treatment resistant partial onset seizures. Subjects with partial onset seizures not fully controlled despite their treatment with 1 to 3 concomitant AEDs were included in this study. The study included an 8 week baseline period to assess seizure frequency. Only subjects who experienced at least 3 seizures/month during the baseline period with no 21-day seizure-free period were randomized in a 1:1 ratio to add-on placebo or cenobamate administered in an oral formulation once daily in the morning. Subjects then entered a 12-week double-blind treatment period, consisting of a 6-week titration phase followed by a 6-week maintenance phase. In maintenance phase, the dose was 200 mg/day.

Blood samples were drawn at the baseline, predose at the start of the titration phase, and on days 15, 29, 43, 57 and 85 after the first dose during the double-blinded treatment period. These samples were analyzed for lamotrigine, levetiracetam, oxcarbazepine, carbamazepine, and valproic acid.

(2) Efficacy and Safety Study—Cenobamate Study 2

This is a multicenter, double-blind, randomized, placebo-controlled dose-response study, with an 8-week prospective baseline and an 18-week double-blind treatment period. Subjects must have had least 8 partial seizures including only simple partial seizures with motor component, complex partial seizures, or secondarily generalized seizures without a seizure-free interval of greater than 25 days any time during the 8-week baseline despite their treatment with 1 to 3 AEDs. Subjects must have had at least 3 of these partial seizures during each of the two consecutive 4-week periods in the baseline period to be randomized to 100, 200 or 400 mg/day cenobamate or placebo (1:1:1:1 ratio) administered as a tablet formulation once daily in the morning. Subjects first entered a 6-week titration followed by a 12-week maintenance phase. Blood samples were drawn at the start of the titration phase, and on day 71 and 99 during the maintenance phase. Samples were analyzed for lamotrigine, lacosamide, levetiracetam, oxcarbazepine, carbamazepine, valproic acid and topiramate.

(3) Safety and PK Study—Cenobamate Study 3

This is an open label multicenter safety and PK study, with a 12-week titration phase followed by an open label maintenance phase (Cenobamate Study 3 was a long-term open label safety and PK study in subjects with POS who received doses up to 400 mg/day). Subjects must have had uncontrolled partial seizures and require additional therapy despite their treatment with at least one AED within the last 2 years. Subsequently, the dose of cenobamate was increased to a maximum dose of 400 mg/day. Blood samples were drawn on day 1, day 29, day 43, day 57, day 71, day 85, and day 99. Samples were analyzed for lamotrigine, levetiracetam, oxcarbazepine, and phenytoin.

3. Data Handling

The information on AED dosing was self-reported, and as a result of that procedure, this information was not consistent between subjects. The data were reviewed, and subjects with missing or incomplete information were not included in these analyses. Records with missing AED concentration or lacking the time of last AED dose were discarded. It would be reasonable to expect a considerable degree of interaction between the individual AEDs: therefore, all data where a subject had been receiving more than one AED in addition to cenobamate in the last 14 days preceding the PK sample were excluded.

4. Software

PopPK analyses were carried out using NONMEM (Version 7.3, ICON Development Solutions, Elicott City, MD, USA) on workstations with Intel® Core. i7 processors, Windows 7 Professional and the GNU gfortran compiler (Version 4.5.0). The NONMEM installation was validated according to a qPharmetra SOP. Post-processing of NONMEM analysis results was carried out in R version 3.2.2.

5. Model Building

The levels of the respective AEDs over time were described using a turnover model with the cenobamate effect included on either the production or the elimination of the observed AED.

6. Simulations

Using the variance-covariance matrix reported by NONMEM to obtain (quasi-)posterior parameter estimate distributions, individual model-based AED concentration-time profiles were obtained.

The results from a population pharmacokinetic modeling analysis are described in Table 1.

TABLE 1

| Simulated Percent Change from Baseline AED Concentration (95% CI) | | | |
|---|---|---|---|
| | 100 mg/day | 200 mg/day | 400 mg/day |
| Carbamazepine | −11 (−16−−7.9) | −21 (−27−−15) | −34 (−43−−25) |
| Lamotrigine | −21 (−28−−16) | −35 (−43−−27) | −52 (−60−−43) |
| Levetiracetam | −3.6 (−13−−1.0) | −7.1 (−24−−2.1) | −13 (−39−−4.1) |
| Oxcarbazepine | 9.5 (−0.5-20) | 9.5 (−0.5-20) | 9.5 (−0.5-20) |
| Phenytoin | 10 (7.1-14) | 23 (15-33) | 60 (36-99) |
| Valproic acid | −5.2 (−9.2−−1.8) | −10 (−17−−3.6) | −19 (−31−−7.0) |

The results from the simulations for the AEDs where significant effects of cenobamate exposure were found are presented. The obtained results are summarized in Table 2.

TABLE 2

| Effect of cenobamate on AED concentrations (AUC) over the 100 to 400 mg/day dose range | | |
|---|---|---|
| Drug | Effect on AED Concentration | Cenobamate Dose |
| Carbamazepine | Reduction by 11-34% | 100-400 mg/day |
| Lamotrigine | Reduction by 21-52% | 100-400 mg/day |
| Levetiracetam | Reduction by 4-13% | 100-400 mg/day |
| Oxcarbazepine | Increased by 10% | 100-400 mg/day |
| Phenytoin | Increase by 10-60% | 100-400 mg/day |
| Valproic acid | Reduction by 5-19% | 100-400 mg/day |

PK parameters (Cmin (ng/mL), Cavg (ng/mL), Cmax (ng/mL) and AUC (ngh/mL)) were calculated using the Bayesian post-hoc model parameters from the final model.

(1) Carbamazepine

The mean reduction of carbamazepine concentrations at the suggested therapeutic cenobamate dose of 100-400 mg/day ranges between 11% and 34%.

(2) Lamotrigine

The mean reduction of lamotrigine concentrations at the suggested therapeutic cenobamate dose of 100-400 mg/day ranges between 21% and 52%.

(3) Levetiracetam

The mean reduction of levetiracetam concentrations at the suggested therapeutic cenobamate dose of 100-400 mg/day ranges between 3.6% and 13%.

(4) Oxcarbazepine

The mean increase in oxcarbazepine concentrations at the suggested therapeutic cenobamate dose of 100-400 mg/day is constant at 9.5%.

(5) Phenytoin

The mean simulated increase of phenytoin concentrations at the suggested therapeutic cenobamate dose of 100-400 mg/day ranges between 10% and 60%.

(6) Valproic Acid

The mean reduction of valproic acid concentrations at the suggested therapeutic cenobamate dose of 100-400 mg/day ranges between 5.2% and 19%.

As a result, combination therapy with cenobamate, and carbamazepine, lamotrigine, levetiracetam, oxcarbazepine, phenytoin or valproic acid resulted in increase or reduction in AED concentration and thus, dose adjustment of those AEDs is necessary when they are used in combination with cenobamate.

What is claimed is:

1. A method for treating a patient who is suffering from epilepsy with co-administering a therapeutically effective amount of (i) [(1R)-1-(2-chlorophenyl)-2-(tetrazol-2-yl-ethyl] carbamate (cenobamate) or a pharmaceutically acceptable salt thereof and (ii) one or two antiepileptic drugs, said method comprising:

modifying the therapeutically effective amount of the antiepileptic drug to adjust AUC of the antiepileptic drug obtained after the co-administration having at least 5% difference to the level of AUC obtained after the administration of antiepileptic drug to the patient without cenobamate or a pharmaceutically acceptable salt thereof, wherein the antiepileptic drug is selected from the group consisting of phenobarbital and phenytoin, and wherein the therapeutically effective amount of cenobamate is achieved by the following titration method:

(1) administering cenobamate to the patient about 12.5 mg once daily for about two weeks;

(2) then administering cenobamate to the patient about 25 mg once daily for two weeks;

(3) then administering cenobamate to the patient about 50 mg once daily for about two weeks; and (4) then increasing the dose in about bi-weekly increments by no more than about 50 mg once daily to a therapeutically effective amount.

2. The method according to claim 1, wherein the therapeutically effective amount of cenobamate is achieved by the following titration method:

(1) administering cenobamate to the patient about 12.5 mg once daily for weeks 1 and 2;

(2) then administering cenobamate to the patient about 25 mg once daily for weeks 3 and 4;

(3) then administering cenobamate to the patient about 50 mg once daily for weeks 5 and 6;

(4) then administering cenobamate to the patient about 100 mg once daily for weeks 7 and 8;

(5) then optionally administering cenobamate to the patient about 150 mg once daily for weeks 9 and 10; and (6) then optionally administering cenobamate to the patient about 200 mg once daily for week 11 and thereafter.

3. The method according to claim 1, wherein the therapeutically effective amount of cenobamate is achieved by the following titration method:

(1) administering cenobamate to the patient about 12.5 mg once daily for weeks 1 and 2;

(2) then administering cenobamate to the patient about 25 mg once daily for weeks 3 and 4;

(3) then administering cenobamate to the patient about 50 mg once daily for weeks 5 and 6;

(4) then administering cenobamate to the patient about 100 mg once daily for weeks 7 and 8;

(5) then administering cenobamate to the patient about 150 mg once daily for weeks 9 and 10; and (6) then administering cenobamate to the patient about 200 mg once daily for week 11 and thereafter.

4. The method according to claim 1, wherein the therapeutically effective amount of cenobamate is achieved by the following titration method:

(1) administering cenobamate to the patient about 50 mg once daily for about two weeks; and (2) then increasing the dose in about bi-weekly increments by about 50 mg once daily to about 200 mg/day once daily, wherein cenobamate is administered for about 6 weeks and the therapeutically effective amount of cenobamate is about 200 mg/day.

5. The method according to claim 1, wherein the therapeutically effective amount of cenobamate is achieved by the following titration method:

(1) administering cenobamate to the patient about 50 mg once daily which is increased with 50 mg once daily per week to about 100 mg/day;

(2) optionally increasing the dose in about weekly increments by about 50 mg once daily per week to about 200 mg/day; and (3) optionally increasing the dose in about weekly increments by about 100 mg/day per week to about 400 mg/day, wherein cenobamate is administered for about 2 weeks, 4 weeks, or 6 weeks depending on therapeutically effective amount of cenobamate which is required and the therapeutically effective amount of cenobamate is about 100 mg/day, about 200 mg/day or about 400 mg/day.

* * * * *